United States Patent [19]

Kristiansen

[11] Patent Number: 5,242,431
[45] Date of Patent: Sep. 7, 1993

[54] SUTURE SLEEVE ASSEMBLY WITH SLIDABLE COMPRESSION COLLAR

[75] Inventor: Jeffrey C. Kristiansen, Simi Valley, Calif.

[73] Assignee: Siemens Pacesetter, Inc., Sylmar, Calif.

[21] Appl. No.: 896,942

[22] Filed: Jun. 11, 1992

[51] Int. Cl.⁵ .................... A61M 25/00; F16J 15/00
[52] U.S. Cl. .................. 604/283; 128/DIG. 26; 285/308; 285/86; 285/334.1; 607/126
[58] Field of Search ........... 128/785, 419 P, DIG. 26; 604/283, 905; 285/305, 308, 309, 382, 391, 330, 334.1, 86

[56] References Cited

U.S. PATENT DOCUMENTS

| | | | |
|---|---|---|---|
| 3,888,523 | 6/1975 | Bartholomew | 285/382 |
| 4,088,349 | 5/1978 | Guest | 285/382 |
| 4,114,626 | 9/1978 | Beran | 128/DIG. 26 |
| 4,114,930 | 9/1978 | Perkins et al. | 285/382 |
| 4,276,882 | 7/1981 | Dickhudt et al. | 128/419 P |
| 4,387,727 | 6/1983 | Sandstrom | 128/784 |
| 4,516,584 | 5/1985 | Garcia | 128/785 |
| 4,526,572 | 7/1985 | Donnan et al. | 604/283 |
| 4,538,623 | 9/1985 | Proctor et al. | 128/784 |
| 4,553,961 | 11/1992 | Pohndorf et al. | 604/175 |
| 4,616,855 | 10/1986 | Ruhle | 285/921 |
| 4,672,979 | 6/1987 | Pohndorf | 128/784 |
| 4,683,895 | 8/1987 | Pohndorf | 128/784 |
| 4,769,897 | 9/1988 | Moseman | 285/382 |
| 5,111,858 | 5/1992 | Aittama et al. | 285/921 |
| 5,131,632 | 7/1992 | Olso | 285/382 |

Primary Examiner—Stephen C. Pellegrino
Assistant Examiner—Gary Jackson
Attorney, Agent, or Firm—Malcolm J. Romano

[57] ABSTRACT

A suture sleeve assembly for gripping and anchoring the lead body of an implantable medical device, such as a cardiac pacemaker, includes a tubular member adapted to receive the lead body. Disposed about the tubular member is a collar movable longitudinally along the tubular member from a first, open position to a second position in which the collar compresses a portion of the tubular member into gripping engagement with the outer surface of the lead body. The collar is fabricated of a material that is stiffer than that from which the tubular member is fabricated.

11 Claims, 3 Drawing Sheets

SUTURE SLEEVE ASSEMBLY WITH SLIDABLE COMPRESSION COLLAR

CROSS REFERENCES TO RELATED APPLICATIONS

This application is related to application Ser. No. 07/639,643, filed Jan. 10, 1991, entitled "Multiple Lead Suture Sleeve," and to application Ser. No. 07/686,095, filed Apr. 16, 1991, entitled "Threaded Suture Sleeve."

FIELD OF THE INVENTION

This invention relates generally to suture sleeves for anchoring the lead bodies of implantable medical devices such as cardiac pacemakers, and more particularly to a suture sleeve assembly for securely gripping and anchoring a lead body without damage thereto.

BACKGROUND OF THE INVENTION

During the implantation of an endocardial lead body, the lead is introduced into the heart using a venous approach, usually from the subclavian or cephalic vein in the shoulder area under the pectoral muscle. To stabilize the lead body at the venous entry site, the lead body is secured to both the vein and to the surrounding fascia tissue. A suture placed around the vein near the lead entry point ties the lead body to the vein, and a suture sleeve around the lead body is used to anchor the lead body to adjacent tissue.

Suture sleeves in present use are generally tubular structures molded out of a soft, implantable elastomer such as silicone. After the lead body is tied to the vein, the sleeve is slid along the lead body to the location at which the lead is to be anchored to the underlying tissue. One or more sutures are then tied around the sleeve to compress it and thereby secure it to the lead body. Circumferential grooves in the outer surface of the sleeve are typically provided for this purpose. The last step is to anchor the sleeve to adjacent body tissue; sutures passed through eyelets formed in a pair of tabs projecting from the sleeve provide the required anchoring.

These existing suture sleeves have several drawbacks. For example, it is difficult for the physician to control the degree to which these sleeves are compressed when they are secured to the lead body. The ligature around the sleeve must be tight enough to prevent the lead body from sliding in the suture sleeve but not so tight as to damage the insulation of the lead body. This is especially important with bipolar coaxial leads because an excessively tight ligature could rupture the lead insulation and cause the outer and inner electrical leads to come into contact with each other, resulting in a short circuit. Overtightened ligatures can also result in electrical lead fractures. These problems are common enough to warrant the inclusion of cautionary information in pacemaker product literature or in notices included in the product packaging regarding the use of anchoring sleeves. It would therefore be desirable to eliminate the need for sutures for compressing the sleeve.

U.S. Pat. No. 4,672,979 discloses another type of suture sleeve comprising an outer, elastomeric tubular sleeve and a relatively stiff collet member. The collet includes a plurality of axially extending legs having inner surfaces that are serrated so as to firmly grip the lead body. In use, the collet and the tubular sleeve are separately threaded onto the lead body. With the collet positioned at the lead body anchoring site, the tubular sleeve is forced over the collet thereby urging the serrated surfaces of the collet inwardly into engagement with the lead body. The assembly is then sutured to surrounding tissue to anchor the lead body.

The suture sleeve of the '979 patent has several disadvantages. The serrations have a tendency to pinch and puncture the outer insulative layer of the lead body. Moreover, because the tubular sleeve and collet are separate elements, during positioning of the collet the tubular sleeve may slide down the lead body due to its lubricity when covered with body fluids. In this event, the suture sleeve installation is substantially complicated.

Accordingly, it is an object of the present invention to provide a suture sleeve for securely gripping and anchoring the lead body of an implantable medical device, such as a cardiac pacemaker, that does not require the use of sutures to compress the sleeve.

It is another object of the present invention to provide a lead body gripping and anchoring suture sleeve that does not damage the lead body.

It is yet another object of the present invention to provide a compressible lead body gripping and anchoring suture sleeve in which the compression of the sleeve is self-limiting so as to prevent lead body damage.

SUMMARY OF THE INVENTION

In accordance with one exemplary embodiment of the present invention, there is provided a suture sleeve assembly for gripping and anchoring the lead body of an implantable medical device including a tubular body having a first longitudinally extending portion and a second longitudinally extending portion, the second portion having concentric inner and outer surfaces. A slidable collar is disposed about the tubular body coaxially therewith, the collar being slidable longitudinally along the tubular body from a first position in which the collar is disposed on the first portion of the tubular body to a second position in which the collar is disposed on the second of the tubular body. In its second position, the collar compresses the outer surface of the second portion of the tubular body to urge the inner surface thereof inwardly whereby the inner surface of the second portion of the tubular body is adapted to grip the lead body.

In accordance with other, more detailed aspects of the invention, retention means projecting outwardly from the tubular body adjacent the first and second portions thereof are provided for preventing removal of the collar from the tubular body. Further, the collar and second portion of the tubular body are so dimensioned that the compression of the second portion of the tubular body is self-limiting. More specifically, the diameter of the outer surface of the second portion is greater than the diameter of the collar bore. These dimensions are so related that the degree of compression can be predetermined and limited in accordance with the type, configuration and size of the lead body. Preferably, the tubular body is fabricated of a soft implantable material such as silicone or polyurethane and the collar is fabricated of an implantable material that is stiffer than the tubular body material. For example, the collar may be fabricated of polysulfone, delrin or a variety of implantable metals or metal alloys.

BRIEF DESCRIPTION OF THE DRAWINGS

Further objects, advantages and features of the invention will become apparent from the detailed description of the preferred embodiments, below, when read in conjunction with the accompanying drawing, in which.

DETAILED DESCRIPTION OF THE PREFERRED EMBODIMENTS

Figure 1:
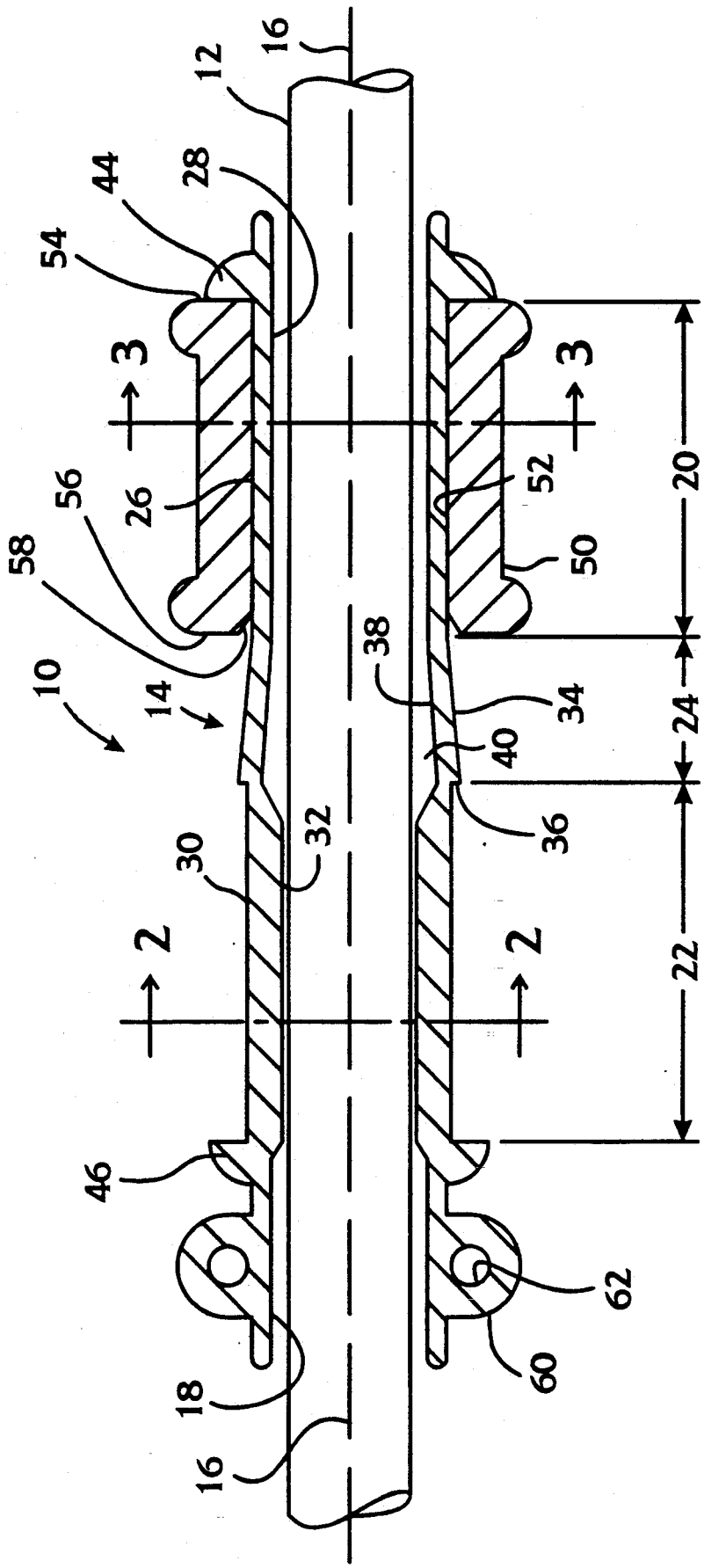
FIG. 1 is an axial cross-section view of a suture sleeve assembly for anchoring the lead body of an implantable medical device in accordance with a preferred embodiment of the present invention, the suture sleeve assembly being shown in its open configuration.
Figure 2:
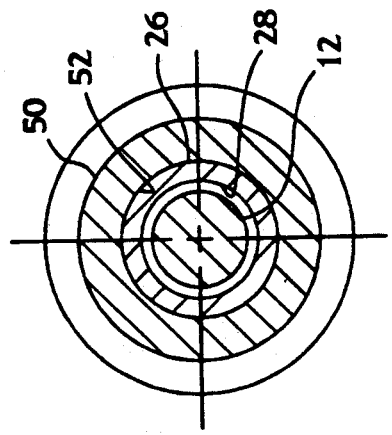
FIGS. 2 and 3 are transverse cross-section views of the assembly of FIG. 1 as seen along the lines 2—2 and 3—3, respectively.
Figure 3:
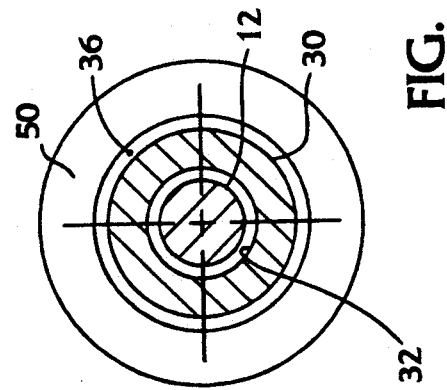

FIGS. 1-4 show a suture sleeve assembly 10 for gripping and anchoring the lead body 12 of an implantable medical device such as a cardiac pacemaker. Because the structures of lead bodies are well known in the art, the details thereof have been omitted from the drawings for the sake of simplicity. The lead body will typically be of the bipolar coaxial type with which the present invention has particular utility. As is known, such lead bodies comprise inner and outer coiled conductors surrounded by an outer tube of soft, implantable insulating material such as silicone.

The suture sleeve assembly 10 includes a tubular member 14 having a central, longitudinal axis 16 and a through bore 18 for receiving the lead body. The tubular member 14 is preferably fabricated of a soft plastic and includes three portions: a first portion 20, a second portion 22 spaced apart longitudinally from the first portion 20, and a third portion 24 interconnecting the first and second portions.

The first portion 20 of the tubular body 14 has generally cylindrical, concentric outer and inner surfaces 26 and 28, respectively. Similarly, the second portion 22 of the tubular body 14 has a generally cylindrical outer surface 30 and a generally cylindrical inner surface 32 concentric with the outer surface. The diameter of the outer surface 30 of the second portion 22 is greater than the diameter of the outer surface 26 of the first portion. The diameter of the inner surface 28 of the second portion 22 is less than the diameter of the inner surface of the first portion. The diameter of the inner surface 28 of the second portion 22 is preferably the same as, or slightly greater, than the outer diameter of the lead body 12 so that the sleeve assembly 10, prior to being secured in place, resists sliding along the lead body when the lead body is held vertically.

The third portion 24 of the tubular member 14 has an outer surface 34 that tapers outwardly, that is, away from the longitudinal axis 18, in the direction from the first portion 20 to the second portion 22 of the tubular body 14 so that the larger diameter end of the tapered portion is adjacent the second portion 22. The outer diameter of the larger end of the tapered surface 34 is greater than the diameter of the outer surface 30 of the second portion 22. At the junction of the tapered surface 34 and the second portion 22 is a radially extending shoulder surface 36. The third or tapered portion 24 of the tubular body has an inner surface 38 which, in accordance with the embodiment under consideration, has a gentle outward taper in the same direction as the taper of the outer surface 34 so that a clearance or relief space 40 is defined between the inner surface 38 and the lead body 12.

Projecting outwardly from the tubular body, proximate the ends thereof, are retainer flanges 44 and 46.

Disposed about the tubular body is a slidable collar 50 having a bore 52 and planar, radially extending ends 54 and 56. The bore 52 has a flared end 58 adjacent the end 56 of the collar.

The tubular body is preferably made of a soft implantable elastomer such as silicone or polyurethane. The collar is preferably fabricated of a harder implantable plastic such as polysulfone or delrin. Alternatively, the collar may be fabricated of an implantable metal or metallic alloy such as titanium, platinum, platinum-iridium or stainless steel.

Figure 4:
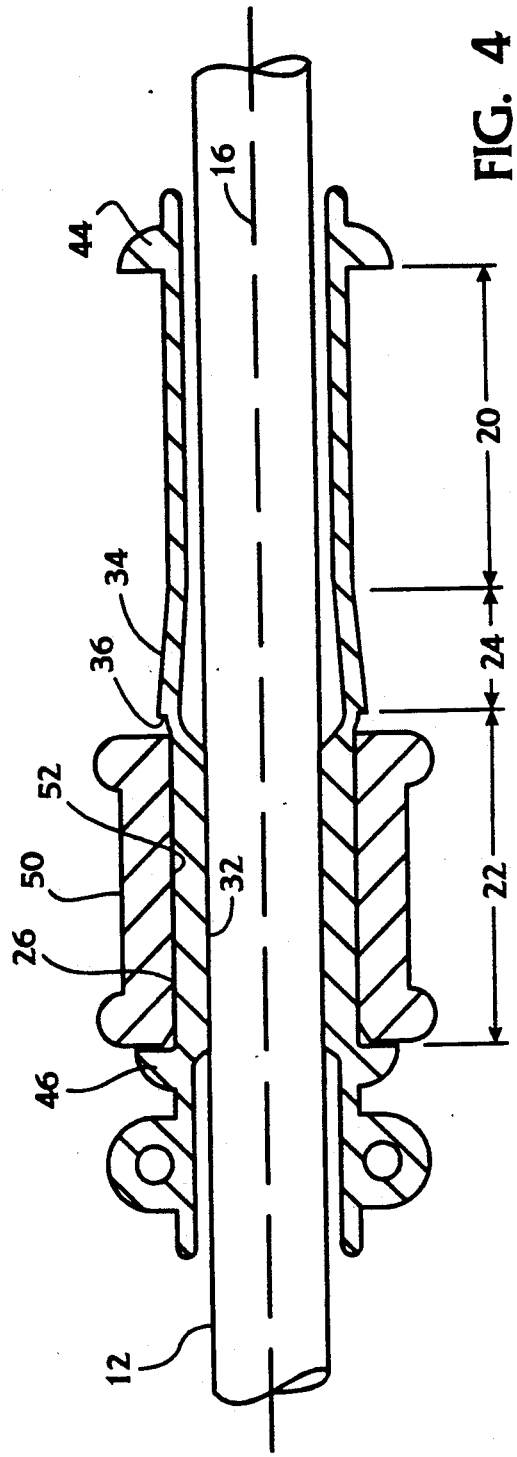
FIG. 4 is an axial cross-section view of the sleeve assembly of FIG. 1 in its closed, lead body-gripping configuration.

FIG. 1 shows the slidable collar 50 in a first or open position in which the collar is on the first portion 20 of the tubular body while FIG. 4 shows the collar 50 in a second or gripping position in which the collar is on the second portion 22 of the tubular body.

A pair of projecting tabs 60 formed integrally with the tubular body include eyelets 62 adapted to receive sutures for tying the suture sleeve assembly 10 to the surrounding tissue.

By way of example only, and not by way of limitation, the suture sleeve assembly 10 in accordance with the embodiment depicted in the drawings may have the following dimensions for a lead body whose outer insulation has a diameter of 0.090 inches:

| First portion 20: | |
|---|---|
| Length: | .425 inches |
| Diameter of outer surface: | .175 inches |
| Diameter of inner surface: | .125 inches |
| Second portion 22: | |
| Length: | .320 inches |
| Diameter of outer surface: | .200 inches |
| Diameter of inner surface: | .100 inches |
| Third tapered portion 24: | |
| Length: | .100 inches |
| Diameter at larger end: | .250 inches |
| Collar 50: | |
| Length: | .300 inches |
| Bore diameter: | .185 inches |

It will be evident that these dimensions can be varied as required to accommodate particular lead body types, configurations and sizes.

Figure 5:
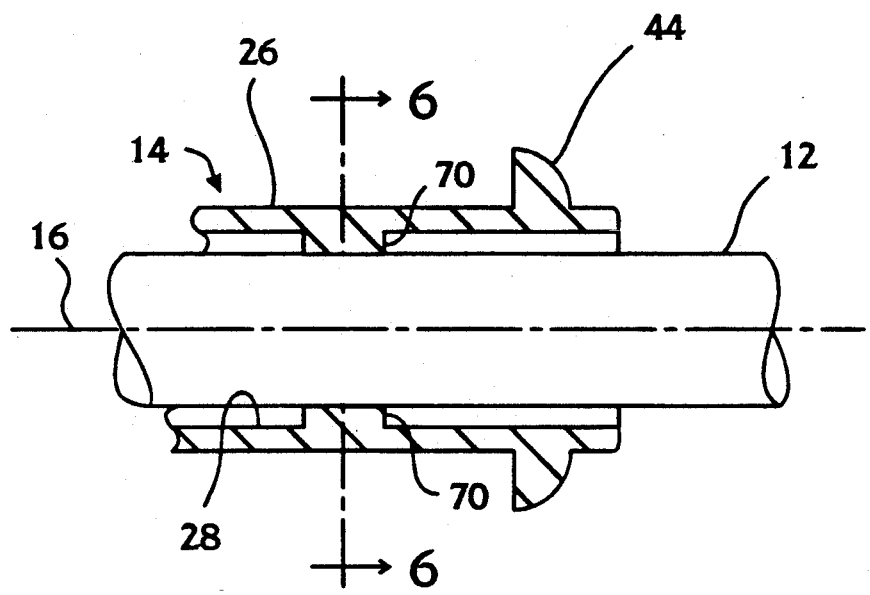
FIG. 5 is an axial cross-section view of a portion of a suture sleeve assembly in accordance with an alternative embodiment of the invention.
Figure 6:
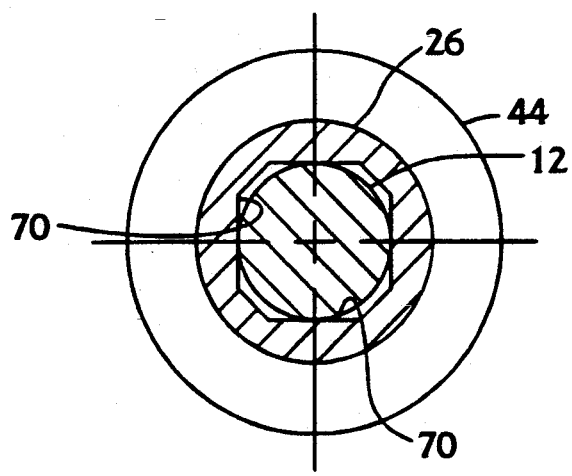
FIG. 6 is a transverse cross-section view of the embodiment of FIG. 5 as seen along the line 6—6.

As already stated, the diameter of the inner surface 32 of the second portion 22 of the tubular body 14 is such relative to the lead body diameter that the sleeve assembly 10 resists sliding along the lead body before being secured in place. FIG. 5 shows an alternative embodiment in which the inner surface 28 of the first portion 20 of the tubular body is provided with flats 70 or equivalent inwardly directed projections dimensioned so that they lightly engage the outer surface of the lead body 12. As a result, the sleeve assembly 10 resists sliding along the lead body when the lead body is held vertically. Such flats or equivalent projections can be used in place of or in combination with an appropriately dimensioned inner surface of the second portion of the tubular body, as already explained.

In use, with the collar 50 in its first or open position as shown in FIG. 1, the sleeve assembly 10 is moved along the lead body to the desired anchoring position. In this connection, it will be appreciated that the collar is retained in the first position by the flange 44 and tapered portion 34. When the sleeve location has been determined the collar is moved past the tapered portion 34 to its second position. The flared portion 58 of the bore facilitates movement of the collar 50 along the tapered portion 34 of the tubular body, the tapered portion 34 being compressed as the collar 50 traverses that portion. Once the collar is past the tapered portion, the tapered portion expands so that with the collar in its second position, shown in FIG. 4, the collar is locked in place by the retainer flange 46 at one end and the shoulder 36 at the other end. Because the outer diameter of the second portion 22 of the tubular body is less than the bore diameter of the collar 50, the second portion of the softer tubular body is compressed into gripping engagement with the lead body. Finally, the suture assembly is anchored in place by suturing the assembly to the surrounding tissue, the eyelets 62 being used for this purpose.

The diameters of the collar bore 52 and second portion 22 of the tubular body 14 are such in relation to the diameter of the lead body 12, that compression of the lead insulation is limited in a manner predetermined by the dimensions chosen. Because compression of the lead body is thus limited, the suture sleeve assembly provides reliable, secure gripping of the lead while preventing damage thereto.

While various modification and alternative constructions of the invention will be obvious to those skilled in the art, only a specific, preferred embodiment thereof has been shown in the drawings and described in detail. It should be understood, however, that there is no intention to limit the invention to the specific form or example illustrated and described. On the contrary, the intention is to cover all modifications, alternative constructions and equivalents falling within the spirit and scope of the invention as defined by the appended claims.

What is claimed is:

1. A suture sleeve assembly for gripping and anchoring the lead body of an implantable medical device, the assembly having a central longitudinal axis and comprising:
   a tubular body including a first, longitudinally extending portion and a second, longitudinally extending portion, the second portion having an outer surface and an inner surface; and
   a slidable collar disposed about the tubular body coaxially therewith, the collar being slidable longitudinally along the tubular body from a first position in which the collar is disposed on the first portion of the tubular body to a second position in which the collar is disposed on the second portion of the tubular body, the tubular body including means for retaining the collar in the first and second positions, the collar, in its second position, engaging the outer surface of the second portion of the tubular body to compress the second portion and urge the inner surface thereof inwardly toward the longitudinal axis whereby the inner surface is adapted to grip the lead body.

2. A suture sleeve assembly, as defined in claim 1, in which the collar has a bore for receiving the tubular body, the bore having a diameter less than the diameter of the outer surface of the second portion of the tubular body.

3. A suture sleeve assembly, as defined in claim 2, in which the first portion of the tubular body includes an outer surface, the outer surfaces of the first and second portions being joined by a surface tapering outwardly relative to the longitudinal axis in the direction from the first portion to the second portion of the tubular body.

4. A suture sleeve assembly, as defined in claim 3, which further includes a radially extending shoulder surface at the junction of the tapering surface and the outer surface of second portion of the tubular body, the shoulder surface preventing movement of the collar from the second position to the first position thereof.

5. A suture sleeve assembly, as defined in claim 3, which further includes retention means projecting from the tubular body at one end thereof adjacent the first portion for preventing removal of the collar from the tubular body, the collar being retained in the first portion thereof by the retention means and the tapering surface.

6. A suture sleeve assembly, as defined in claim 3, which includes retention means projecting outwardly from the tubular body adjacent the first and second portions thereof for preventing removal of the collar from the tubular body.

7. A suture sleeve assembly, as defined in claim 1, further including means for attaching the assembly to adjacent tissue.

8. A suture sleeve assembly, as defined in claim 1, in which the tubular body is fabricated of a soft, implantable material and the collar is fabricated of an implantable material that is stiffer than the tubular body material.

9. A suture sleeve assembly, as defined in claim 8 in which the tubular body is fabricated of a material selected from the group consisting of silicone and polyurethane and the collar is fabricated of a material selected from the group consisting of polysulfone, delrin, titanium, platinum, platinumiridium and stainless steel.

10. A suture sleeve assembly, as defined in claim 1, in which the inner surface of the second portion of the tubular body has a diameter substantially equal to the outer diameter of the lead body whereby the suture sleeve assembly resists movement along the lead body.

11. A suture sleeve assembly, as defined in claim 1, in which the first portion of the tubular body has an inner surface, said first portion including means projecting inwardly from the inner surface thereof for engaging the outer surface of the lead body, whereby the suture sleeve assembly resists movement along the lead body.

* * * * *

UNITED STATES PATENT AND TRADEMARK OFFICE
CERTIFICATE OF CORRECTION

PATENT NO. : 5,242,431
DATED : September 7, 1993
INVENTOR(S) : Jeffrey C. Kristiansen It is certified that error appears in the above-indentified patent and that said Letters Patent is hereby corrected as shown below:

In claim 6, col. 6, line 30, delete "claim 3" and insert therefor --claim 1--.

In claim 9, col. 6, line 48, delete "platinumiridium" and insert therefor --platinum-iridium--.

Signed and Sealed this

Sixteenth Day of May, 1995

Attest:

BRUCE LEHMAN

*Attesting Officer*  *Commissioner of Patents and Trademarks*